United States Patent [19]

Slaugh et al.

[11] 4,306,101

[45] Dec. 15, 1981

[54] OLEFIN HYDRATION PROCESS

[75] Inventors: Lynn H. Slaugh; Carl L. Willis, both of Houston, Tex.

[73] Assignee: Shell Oil Company, Houston, Tex.

[21] Appl. No.: 204,677

[22] Filed: Nov. 5, 1980

[51] Int. Cl.³ .............................................. C07C 29/04
[52] U.S. Cl. .................................... 568/899; 568/835
[58] Field of Search ................................ 568/899, 835

[56] References Cited

U.S. PATENT DOCUMENTS

| | | | |
|---|---|---|---|
| 2,070,258 | 2/1937 | Coleman et al. | 568/899 |
| 2,144,750 | 1/1939 | Bent | 568/899 |
| 2,477,380 | 7/1949 | Kreps et al. | 568/899 |
| 3,257,469 | 6/1966 | Kovach | 568/899 |

FOREIGN PATENT DOCUMENTS 256967  3/1963  Australia .............................. 568/835

*Primary Examiner*—Joseph E. Evans

[57] ABSTRACT

A process is disclosed for hydrating olefins to alcohols using a very active catalyst comprising an alpha-hydroxysulfonic acid prepared by reacting a carbonyl compound with sulfur dioxide and water.

10 Claims, No Drawings

OLEFIN HYDRATION PROCESS

FIELD OF THE INVENTION

This invention relates to a process for the hydration of unsaturated compounds utilizing as a catalyst an alpha-hydroxysulfonic acid.

BACKGROUND OF THE INVENTION

The hydration of olefins utilizing as catalysts sulfuric and sulfonic acids is known in the art, see for example British patent specification No. 1,518,461 issued July 19, 1978. The use of the conventional sulfuric acid and sulfonic acid catalysts have the drawback that certain by-products such as sulfates and ketones are produced. The use of the alpha-hydroxysulfonic acids of the instant invention minimizes these by-products as well as provides a more active catalyst.

SUMMARY OF THE INVENTION

The present invention provides for a process for the hydration of an olefin by contacting said olefin with water and a catalyst comprising an alpha-hydroxysulfonic acid. The alpha-hydroxysulfonic acid is prepared by reacting a carbonyl compound with sulfur dioxide and water. The instant process is suitable for the production of all ranges of alcohols from detergent range alcohols down to ethanol. The instant invention is particularly suited for the production of the lower carbon numbered alcohols as for example $C_2$ through $C_5$ alcohols, in particular for the production of isopropanol from propylene. The alpha-hydroxysulfonic acid catalysts of the instant invention are more active than traditional sulfuric or sulfonic acid catalysts and minimize the production of by-products such as for example sulfates and/or ketones.

DESCRIPTION OF THE PREFERRED EMBODIMENTS

The alpha-hydroxysulfonic acids used as catalysts in the instant olefin hydration process are prepared by reacting a carbonyl compound with sulfur dioxide and water according to the following general equation.

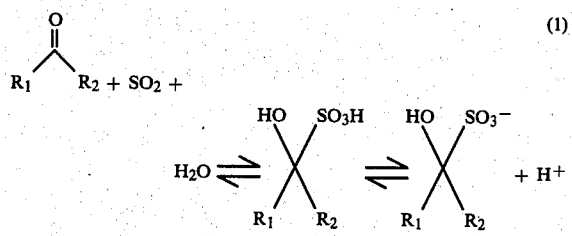

where $R_1$ and $R_2$ are individually hydrogen or hydrocarbyl with up to about 7 carbon atoms. Preferably the hydrocarbyl is unsubstituted or substituted alkyl with up to about 7 carbon atoms.

Illustrative examples of carbonyl compounds useful to prepare the alpha-hydroxysulfonic acids used in this invention are found where $R_1 = R_2 = H$ (formaldehyde)
$R_1 = H$, $R_2 = CH_3$ (acetaldehyde)
$R_1 = H$, $R_2 = CH(CH_3)_2$ (i-butyraldehyde)
$R_1 = H$, $R_2 = CCHCHCHO$ (furfural)

-continued $R_1 = H$, $R_2 = C(CH)_4C(OH)$ (salicylaldehyde)
$R_1 = H$, $R_2 = C(CH)_4CH$ (benzaldehyde)
$R_1 = R_2 = CH_3$ (acetone)
$R_1 = CH_3$, $R_2 = CH_2CH_3$ (methyl ethyl ketone)
$R_1 = CH_3$, $R_2 = CHC(CH_3)_2$ (mesityl oxide)
$R_1 = CH_3$, $R_2 = CH_2CH(CH_3)_2$ (methyl i-butyl ketone)
$R_1$, $R_2 = (CH_2)_5$ (cyclohexanone)
or $R_1 = CH_3$, $R_2 = CH_2Cl$ (chloroacetone)

A unique feature of these acids is the easy reversibility of the acid formation according to equation (1). That is, when heated sulfur dioxide is liberated and the solution becomes neutral. Decreasing the sulfur dioxide pressure for this system induces the same effect. This reversibility provides for the method utilized to remove unutilized acid from the reaction streams. By increasing the temperature or lowering the pressure, the sulfur dioxide can be driven off leaving the carbonyl compound and water. These latter materials can then be removed by conventional means, such as distillation.

Various olefinically unsaturated compounds are hydrated by the present invention. Such compounds are linear, branched or cyclic and are alpha or internal olefins. Suitable compounds are the $C_2$ to $C_{22}$ monoolefinically unsaturated hydrocarbons. The instant process is as applicable to the detergent range olefins, $C_8$ through $C_{22}$, as it is for the lower ranged olefins, $C_2$ through $C_7$. The invention is particularly suited for the lower range $C_2$ through $C_5$ olefins. Mixtures of olefins may be used. Specific examples include ethylene, propylene, butenes, pentenes, hexenes, cyclohexenes, heptenes, octenes, nonenes, dodecenes, pentadecenes, octadecenes, etc. The present invention is particularly advantageous for hydrating propylene to isopropanol. Olefinically unsaturated compounds in admixture with non-olefinic material, e.g. alkanes are also used, and a useful feedstock for the present invention is a socalled BB or butane/butene stream which is mainly a mixture of isobutane with isomeric butenes. The products of the present invention are the alcohols corresponding to the hydration products of the olefinically unsaturated materials used.

The amounts of initial reactants used in the present invention will vary between wide limits. The moles of water initially present should be equal at least to the moles of unsaturated bonds in the olefin to be hydrated. The molar ratio of olefin to water will range from about 1:1 to about 1:50, preferably from about 1:1 to about 1:20, and most preferably from about 1:1 to about 1:10. The molar ratio of alpha-hydroxysulfonic acid to olefin will range from about 1:10 to about 5:1, preferably from about 1:100 to about 2:1.

The temperature at which the reaction is carried out will depend on severable variables. One significant variable would be the specific reactant alcohol combination utilized. The higher molecular weight olefin and alcohols would require higher temperatures in order to maintain reasonable viscosities of the reacting and reactant materials. The particular alpha-hydroxysulfonic acid utilized will also determine reaction temperatures and pressures. The reaction temperatures and pressure chosen should be such as to maintain a high proportion of alpha-hydroxysulfonic acid in the reaction mixture. Temperatures will range from about $-20°$ C. to about $200°$ C., preferably from about $0°$ C. to about $100°$ C.

Preferred pressures range from about 0.5 atmospheres to about 5 atmospheres. The utilization of the lighter molecular weight alpha-hydroxysulfonic acids will result in more optimal utilization of higher temperatures than would the utilization of the higher molecular weight acids. For example, alpha-hydroxymethanesulfonic acid begins to lose some of its efficiency above about 100° C. (at one atmosphere) because of the equilibrium shift above this temperature to the component parts, whereas alpha-hydroxyethanesulfonic acid begins to lose some of its efficiency above about 40° C. (at one atmosphere). Contact times will range from about 0.01 hours to about 100 hours, preferably from about 0.1 to about 50 hours, although other times are not to be ruled out in the process of the invention, longer times being uneconomical.

The contact of the olefin-containing hydrocarbon phase with the aqueous acid-containing phase involves intimate mixing of two immiscible phases by techniques that are well-known in the art.

Inert solvents may also be utilized in the process of the present invention for those reasons that solvents are typically used in hydration reactions. For example, non-polar organic solvents such as alkanes can be utilized to lower the viscosity of the reactant olefin component. Organic solvents which possess both hydrocarbon and water solubility are also used. These latter materials comprise for example alcohols, ethers, ketones, acids, sulfones, etc. Examples of art useful solvents that can be utilized in the process of the instant invention are disclosed in U.S. Pat. No. 2,995,609 issued Aug. 8, 1961; U.S. Pat. No. 3,257,469 issued June 21, 1966, British patent specification No. 973,832 issued Oct. 28, 1964, and others.

The reaction product is worked up by any convenient technique. For example, the hydration reaction product mixture can be subjected to vacuum to strip off the sulfur dioxide from the alpha-hydroxysulfonic acid, and then subsequently stripped by conventional techniques to remove unreacted olefinically unsaturated compounds, carbonyl compounds, and any other non-olefinic material present. The removed material may be recycled directly to the hydration reactor or the carbonyl compounds can be extracted and later combined with $SO_1$ and water to form the alpha-hydroxysulfonic acid which is then recycled to the hydration reactor. The stripped reaction product may then be distilled to produce an alcohol product.

The invention will be illustrated by reference to the following illustrative embodiments which are provided for illustration and are not to be construed as limiting the invention.

ILLUSTRATIVE EMBODIMENTS

In a typical preparation of an alpha-hydroxysulfonic acid, in particular alpha-hydroxymethanesulfonic acid, about 30 grams of sulfur dioxide were condensed (dry ice/acetone bath) into a 200 cc Fisher-Porter pressure bottle. The reaction vessel was opened and slightly less than one equivalent of aqueous formaldehyde solution (37% W $H_2CO$) was added. The pressure bottle was sealed and the mixture warmed to room temperature. The mixture was stirred vigorously overnight and then vented ($SO_2$) to the atmosphere. Analysis of the resulting aqueous phase (potentiometric titration with $NaOH/H_2O$) typically found about 5 M alpha-hydroxymethanesulfonic acid and a trace of sulfur oxide. The solution could be stored for up to about four weeks in the pressure bottle without loss in activity.

In a typical experiment about 11 grams (260 mmol) of propylene, 66 grams (3600 mmol) of water and 270 mmol of acid catalysts were added to a 300 cc Hastelloy B autoclave. The reactor was heated to 85° C. for the indicated time and initial pressure. Analysis was by GPC (80°→225° C.; 12'; 5% C20M Nickel Column) using diglyme as an external standard. The results are shown in Table I below. The sulfuric acid catalyst was noted to form sulfates and the para-toluene sulfonic acid catalyst was noted to have oxidized isopropyl alcohol to acetone. Neither of these by-products was noted with the alpha-hydroxysulfonic acid catalyst.

| Acid Catalyst | Time (hr.) | Initial Press. (psi) | Yield of Isopropyl Alcohol (Mol %) |
|---|---|---|---|
| α-hydroxymethane sulfonic acid | 2 | 322 | 11.7 |
| α-hydroxymethane sulfonic acid | 2 | 275 | 8.3 |
| α-hydroxymethane sulfonic acid | 14 | 330 | 9.8 |
| $SO_2/H_2O$ Control | 2(80° C.) | 500 | 0.2 |
| p-toluene sulfonic acid | 2 | 380 | 3.8 |
| $H_2SO_4$ | 2 | 365 | 4.6 |

Repeating the above experiment on, for example, 1-pentene and 1-dodecene utilizing α-hydroxymethane sulfonic acid as the catalyst would product a significant yield of the corresponding alcohols.

We claim:

1. A process for the preparation of alcohols which comprises reacting an olefinically unsaturated hydrocarbon with water in the presence of an alpha-hydroxysulfonic acid prepared by reacting a carbonyl compound of the general formula $R_1R_2CO$ wherein $R_1$ and $R_2$ are individually hydrogen or hydrocarbyl of up to about 7 carbon atoms with sulfur dioxide and water.

2. The process of claim 1 wherein the initial molar ratio of olefinically unsaturated hydrocarbon to water ranges from about 1:1 to about 1:50 and the initial molar ratio of acid to olefinically unsaturated hydrocarbon ranges from about 1:10 to about 5:1.

3. The process of claim 2 wherein the initial molar ratio of hydrocarbon to water ranges from about 1:1 to about 1:20 and the initial molar ratio of acid to hydrocarbon ranges from about 1:100 to about 2:1.

4. The process of claim 3 wherein the initial molar concentration of hydrocarbon to water ranges from about 1:1 to about 1:10.

5. The process of claims 1, 2, 3 or 4 wherein the olefinically unsaturated hydrocarbon has a carbon number ranging from 2 to about 22.

6. The process of claims 1, 2, 3 or 4 wherein the olefinically unsaturated hydrocarbon has a carbon number ranging from 2 to about 7.

7. The process of claims 1, 2, 3 or 4 wherein the olefinically unsaturated hydrocarbon is propylene.

8. The process of claims 1, 2, 3 or 4 wherein the unsaturated hydrocarbon is propylene and the alpha-hydroxysulfonic acid is alphahydroxymethanesulfonic acid.

9. The process of claims 1, 2, 3 or 4 wherein the process is carried out at a temperature ranging from about −20° C. to about 200° C.

10. The process of claims 1, 2, 3 or 4 wherein the process is carried out at a temperature ranging from about 0° C. to about 100° C.

* * * * *